(12) United States Patent
Cherciu

(10) Patent No.: US 6,433,451 B1
(45) Date of Patent: Aug. 13, 2002

(54) METHOD AND ELECTRIC MOTOR WITH ROTATIONAL STATOR

(76) Inventor: Traian Cherciu, 426 De Witt Ave., Belleville, NJ (US) 07109

( * ) Notice: Subject to any disclaimer, the term of this patent is extended or adjusted under 35 U.S.C. 154(b) by 0 days.

(21) Appl. No.: 09/416,747

(22) Filed: Oct. 13, 1999

(51) Int. Cl.[7] .......... H02K 16/00; H02K 16/02; H02K 23/60; H02K 21/26; H02K 21/38; H02K 23/04
(52) U.S. Cl. .......... 310/115; 266/114; 266/74; 266/136; 266/148; 266/143
(58) Field of Search ............. 36/191, 115; 310/74, 310/266, 143, 148

(56) References Cited

U.S. PATENT DOCUMENTS

| 4,084,445 A | * | 4/1978 | Erwin | 310/115 |
| 4,229,689 A | * | 10/1980 | Nickoladze | 322/32 |
| 4,516,047 A | * | 5/1985 | Duverger | 310/230 |
| 5,357,180 A | * | 10/1994 | Speicher | 318/49 |
| 6,153,959 A | * | 11/2000 | Lorenzo | 310/162 |

* cited by examiner

Primary Examiner—Nestor Ramirez
Assistant Examiner—Julio R. Gonzalez

(57) ABSTRACT

An electric composite rotating machine haveing two rotors, capable of developing mechanical power and of runing on two rotational direction at selfadjutable speeds, of differential type, with 40% increase of output, doubling the torque at 30% reduction of used electrical energy.

2 Claims, 3 Drawing Sheets

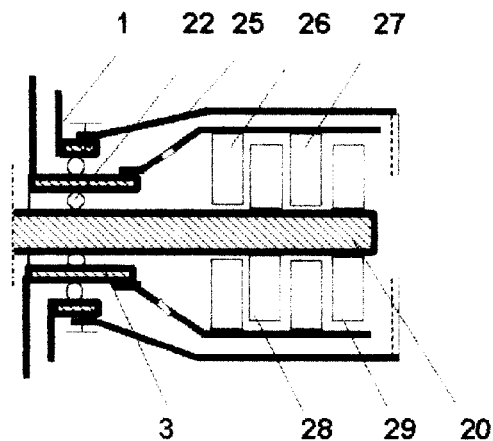
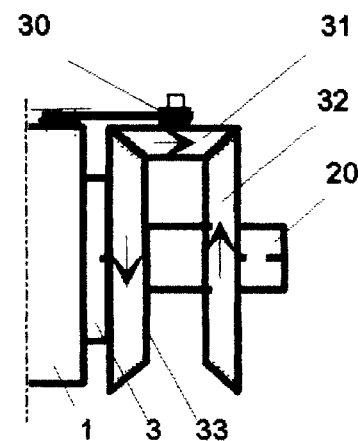
fig. 3
fig. 4
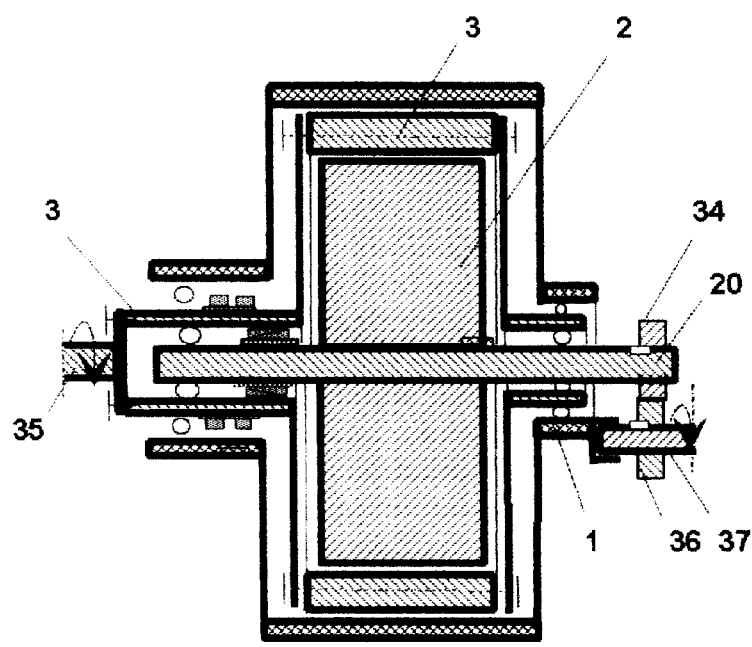
fig. 5

METHOD AND ELECTRIC MOTOR WITH ROTATIONAL STATOR

BACKGROUND OF INVENTION

This invention concerns an electrical motor to be used in various manufacturing activities and transportation.

The existing electrical motor with the coiled stator and coiled rotor that is energized through a distributor, has the following disadvantages:

limited output that can not be exceeded;

the use of the existing electrical motor is limited by the active torque that has only a one way rotational direction;

energy waste due to the stationary stator.

The first objective is to present the principal elements that differenciate the new electrical motor with mobile stator from the existent electrical motor.

The second objective is to describe the governing principle of operation of the new electrical motor.

The other objectives are to illustrate the advantages of the new electrical motor.

FIG. 3 shows an alternative of mechanically coupling between the new engine and the electrical devices that operate with a two way rotational direction, such as: fans, centrifugal pumps, etc.

FIG. 4 shows the principal components of a mechanically coupling device for one a way rotating device.

FIG. 5 shows the principal components of mechanical coupling for various means of transportation, differential type, such as an autovehicle without mechanical differential.

DESCRIPTION OF THE PREFERED EMBODIMENT

Figure 1:
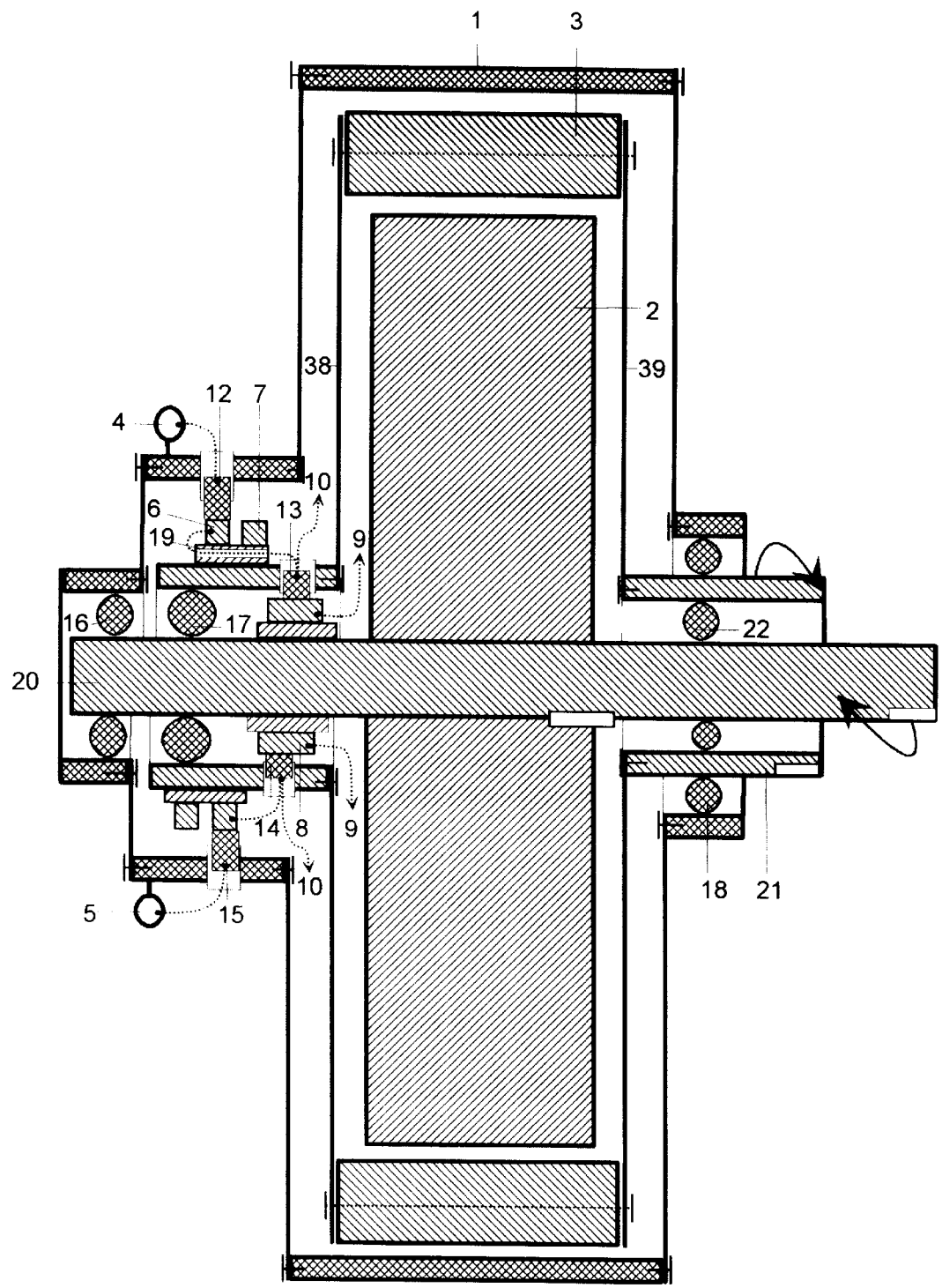
FIG. 1 illustrates the principal parts of the direct current energizing source for new electrical motor with mobile stator.

FIG. 1 illustrates only the new and innovative physical components for building the proposed motor and the corresponding electrical diagram: a frame cover 1, a rotor classic coiled 2, a mobile stator classic coiled with rotation in opposite way from the rotor 3, two electrical connectors 4 and 5, two rings rotor 6 and 7 for energization mobile stator coils 10 (not showed), an electrical distributor 8, for energization rotor coils 9 (not showed), two mobile contact brushes 13 and 14 for distributor, two insulating bushes 11 and 19, four bearings 16, 17, 18 and 22, a mechanically coupling axis for one way of rotation 20 and another mechanically coupling axis for opposite way of rotation 21.

Figure 2:
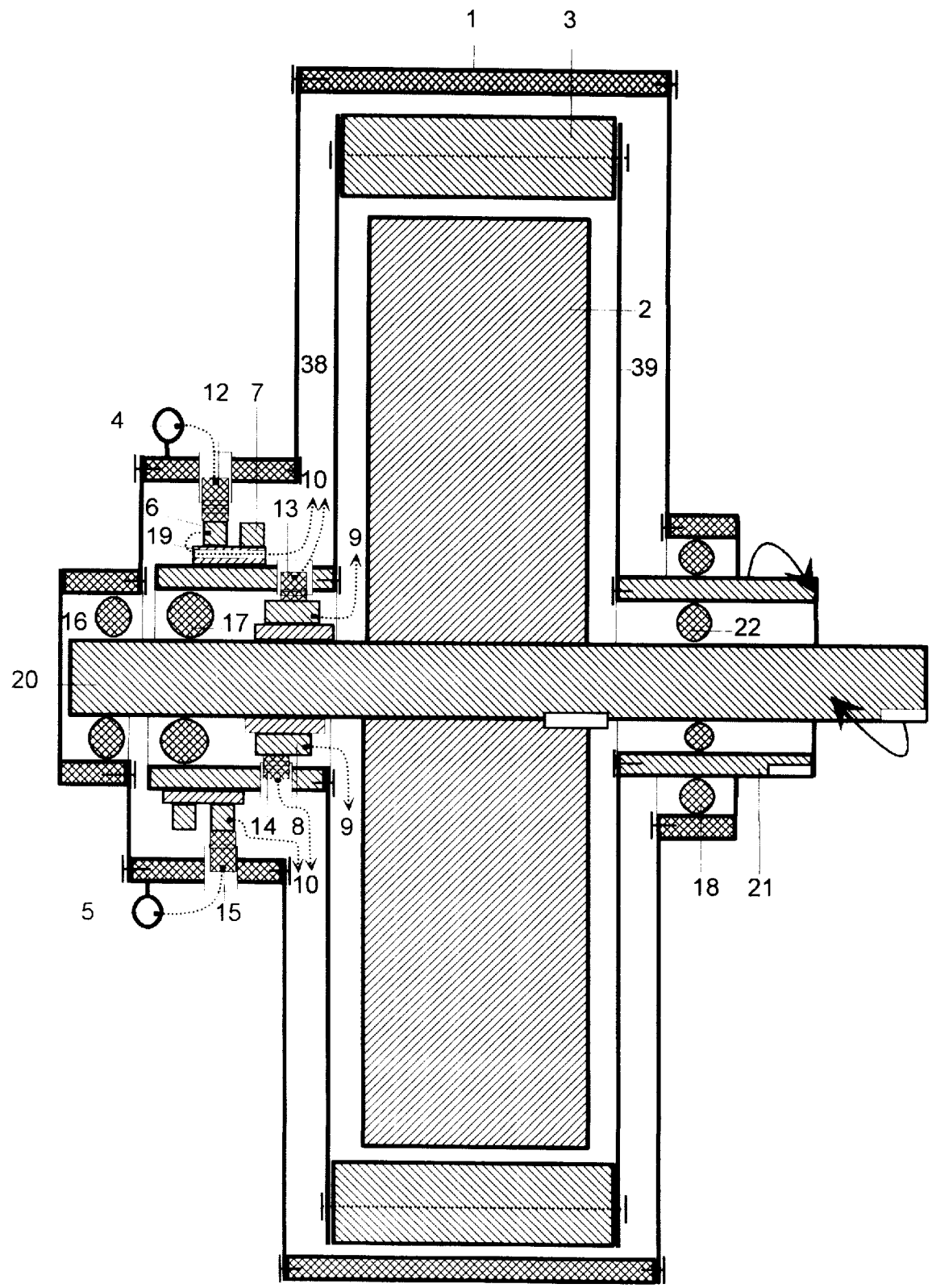
FIG. 2 illustrates the principal components of alternative current energizing source.

FIG. 2 illustrates the same components as shown in FIG. 1, with the main difference that pertains to energization the motor coils by a A.C. source, thus the new points for coupling of the mobile stator coils are 23 and 24.

FIG. 3 shows an example of a mechanically coupling that can be used on such devices that require two way rotation (for example: fans, centrifugal pumps etc.), thus two groupings of fans 26 and 27 rotating in the first way and other two groupings 28 and 29 rotating in the opposite way FIG. 4 illustrates the components included in a mechanical coupling between the mobile stator and rotor for obtaing a torque twice as big when there is only one way rotation thus three conic gears 31, 32 and 33 and a supporting base 30 for coupling gear (31).

FIG. 5 illustrate the principal parts of an adaptor for the differential rotation speed between mobile stator and rotor, for autovehicle train, thus gears 34 and 36 and two semiaxis 35 and 37.

The advantages of the new motor with a mobile stator are following:

Up to 40% higher output than the classical version that has a fixed stator;

By reducing the period of the cycle, there is a corresponding 30% increase of efficiency;

Increasing of the torque by a factor of two;

Autoadjustible at different rotational speed of the mobile stator versus rotor, It can be used to propel different means of transportation without a mechanical differential.

---

FORMULAS REFRESHER $F = m\ a$   F=force;   m=mass;   a=acceleration
$E = F\ s$   E=energy;   s=space (linear displacement)
$s = at^2/2 = Ft^2/2m$   t=time
$t = (ms/F)^{1/2}$
$t_n/t_c = [\{ms/F\}^{1/2}]/[(ms/2F)^{1/2}] = 0.707$   $t_n$ = new time ; $t_c$ = classic time
$P = UI$   P=electric power;   U=electric voltage   I=electric current
$E = Pt = UIt$   E=electric energy
$E_{ic} = Pt_c$   $E_{ic}$=input energy for clasic electric motor; $t_c$=time/period for classic electric motor
$E_{in} = Pt_n$   $E_{in}$=input energy for new electric motor; $t_n$=time/period for new electric motor
New Diagrams
$E_{oc} = E_{on}$
   $E_{oc}$=output energy for classic electric motor
   $E_{on}$=output energy for new electric motor
at the same output energy,
- energy efficiency is η:
$\eta\ (\%) = E_{ic}/E_{in} = Pt_c/Pt_n = t_c/t_n = 100(1/0.707) = 142\%$

---

I claim:

1. A method for improvement of an electric motor characterized by increased power, increased torque and reduced electrical energy consumption, said electric motor comprised of a housing, two rotatable assemblies enclosed within the housing, the first rotatable assembly a rotor, the second rotatable assembly a stator, comprising the steps of:

a. disconnecting the stator from the housing;

b. providing support to the stator and rotor with means of suspension;

c. suspending the stator free from the housing for rotation in a direction opposite of the rotor under influence of the electromagnetic fields developed during rotation;

d. providing the stator with a tubular output shaft concentric with a rotor output shaft having a common central axis;

e. providing separate electrical means for electrical feeding of the stator and rotor;

f. providing the motor with mechanical means for changing the rotational direction of either the rotor or stator for the purpose of doubling torque and increasing the output power on one rotational direction such that the desired output achieved are 30% reduction of electrical energy consumption; 40% increase of output power corresponding to mechanical work produced on a shorter cycle period; twofold increase of desired torque or output power.

2. An improved electric motor characterized by increased power, increased torque and reduced electrical energy consumption, comprised of a housing, two rotatable assemblies enclosed within the housing, the first rotatable assembly a rotor, the second rotatable assembly a stator, the rotor and stator supported by separate suspension means for rotation in opposite directions around a common central axis under influence of the electromagnetic fields developed during rotation; said rotatable stator assembly further comprising a stator right frame tubular extended outside the housing concentric with a rotor output shaft, a stator left frame tubular extended with means to provide separate electrical feeding to the stator and rotor.

* * * * *